US010772834B2

(12) United States Patent
Ono et al.

(10) Patent No.: US 10,772,834 B2
(45) Date of Patent: Sep. 15, 2020

(54) LIPOSOME COMPOSITION AND METHOD FOR PRODUCING SAME

(71) Applicant: FUJIFILM Corporation, Tokyo (JP)

(72) Inventors: Makoto Ono, Ashigarakami-gun (JP); Kohei Ono, Ashigarakami-gun (JP); Takeshi Matsumoto, Ashigarakami-gun (JP); Mikinaga Mori, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 50 days.

(21) Appl. No.: 15/474,644

(22) Filed: Mar. 30, 2017

(65) Prior Publication Data
US 2017/0202774 A1 Jul. 20, 2017

Related U.S. Application Data

(60) Division of application No. 15/336,158, filed on Oct. 27, 2016, now abandoned, which is a continuation of application No. PCT/JP2015/062984, filed on Apr. 30, 2015.

(30) Foreign Application Priority Data

Apr. 30, 2014 (JP) ................................ 2014-094141

(51) Int. Cl.
A61K 9/127 (2006.01)
A61K 31/7068 (2006.01)
A61K 47/28 (2006.01)
B82Y 5/00 (2011.01)
A61K 47/24 (2006.01)

(52) U.S. Cl.
CPC ............ *A61K 9/127* (2013.01); *A61K 9/1278* (2013.01); *A61K 31/7068* (2013.01); *A61K 47/24* (2013.01); *A61K 47/28* (2013.01); *B82Y 5/00* (2013.01)

(58) Field of Classification Search
CPC ............................... A61K 9/127; A61K 9/1278
See application file for complete search history.

(56) References Cited

U.S. PATENT DOCUMENTS

| 4,970,074 | A | * | 11/1990 | Fiechtner | ............... | A61K 9/127 424/450 |
| 5,049,392 | A | * | 9/1991 | Weiner | .................. | A61K 9/1278 264/4.1 |
| 5,077,056 | A | * | 12/1991 | Bally | .................... | A61K 9/1277 424/450 |
| 5,094,854 | A | | 3/1992 | Ogawa et al. | | |
| 5,227,170 | A | * | 7/1993 | Sullivan | .................. | A61K 31/70 424/417 |
| 5,393,530 | A | * | 2/1995 | Schneider | ............ | A61K 9/1278 264/4.3 |
| 5,540,935 | A | * | 7/1996 | Miyazaki | ............. | A61K 9/1271 424/450 |
| 6,261,597 | B1 | * | 7/2001 | Kurtz | ................... | A61K 9/1275 424/450 |
| 2005/0169980 | A1 | * | 8/2005 | Allen | ..................... | A61K 9/127 424/450 |
| 2005/0249795 | A1 | * | 11/2005 | Zhang | .................. | A61K 9/1272 424/450 |
| 2007/0166368 | A1 | * | 7/2007 | Singh | .................. | A61K 9/0019 424/450 |
| 2010/0021531 | A1 | * | 1/2010 | Yoshino | ................. | A61K 9/127 424/450 |

FOREIGN PATENT DOCUMENTS

| CN | 101822669 | * | 9/2010 |
| EP | 0 565 361 A1 | | 10/1993 |
| EP | 0 565 361 B1 | | 10/1993 |
| JP | 02-001404 A | | 1/1990 |
| JP | 06-009374 A | | 1/1994 |
| JP | 2007-536247 A | | 12/2007 |
| JP | 2013-022482 A | | 2/2013 |
| JP | 2013-508315 A | | 3/2013 |
| JP | 2013-126953 A | | 6/2013 |

(Continued)

OTHER PUBLICATIONS

Zhou, Qinmei, et al. "Preparation and characterization of gemcitabine liposome injections." Die Pharmazie-An International Journal of Pharmaceutical Sciences 67.10 (2012): 844-847.*

Cortesi, Rita. "Preparation of liposomes by reverse-phase evaporation using alternative organic solvents." Journal of microencapsulation 16.2 (1999): 251-256.*

Celia, Christian, et al. "Improved in vitro anti-tumoral activity, intracellular uptake and apoptotic induction of gemcitabine-loaded pegylated unilamellar liposomes." Journal of nanoscience and nanotechnology 8.4 (2008): 2102-2113.*

Xu, Hongtao, et al. "Development of high-content gemcitabine PEGylated liposomes and their cytotoxicity on drug-resistant pancreatic tumour cells." Pharmaceutical research 31.10 (2014): 2583-2592.*

(Continued)

*Primary Examiner* — Bethany P Barham
*Assistant Examiner* — Peter Anthopolos
(74) *Attorney, Agent, or Firm* — Sughrue Mion, PLLC

(57) ABSTRACT

Provided are a liposome composition in which an osmotic pressure of an inner water phase is 2-fold to 8-fold relative to the osmotic pressure of an outer water phase, and which encapsulates a water-soluble drug in a dissolved state, and also exhibits excellent preservation stability; and a method for producing the same. According to the present invention, it is possible to provide a liposome composition, including liposomes obtained from lipids dissolved and emulsified in an organic solvent, each of which has an inner water phase and an aqueous solution which constitutes an outer water phase and in which the liposomes are dispersed, in which each of the liposomes encapsulates a water-soluble drug in a dissolved state, and an osmotic pressure of the inner water phase is 2-fold to 8-fold relative to the osmotic pressure of the outer water phase; and a method for producing the same.

2 Claims, 3 Drawing Sheets

(56) References Cited

FOREIGN PATENT DOCUMENTS

| JP | 2013-526563 | A | 6/2013 |
|---|---|---|---|
| WO | 2005/107712 | A1 | 11/2005 |
| WO | 2007/005754 | A2 | 1/2007 |
| WO | 2011-047689 | A2 | 4/2011 |
| WO | 2011-047689 | A3 | 4/2011 |
| WO | 2011/144745 | A2 | 11/2011 |
| WO | 2011/144745 | A3 | 11/2011 |

OTHER PUBLICATIONS

Office Action dated Jun. 27, 2017, from the Japanese Patent Office in counterpart Japanese Application No. 2016-516407.
Extended European Search Report dated Jan. 2, 2017, from the European Patent Office in the corresponding European Application No. 15786541.1.
International Preliminary Report on Patentability issued from the International Bureau in counterpart International Application No. PCT/JP2015/062984, dated Nov. 10, 2016.
International Search Report of PCT/JP2015/062984, dated Jun. 9, 2015 [PCT/ISA/210].
Written Opinion of PCT/JP2015/095984, dated Jun. 9, 2015 [PCT/ISA/237].
Communication dated May 13, 2020, from European Patent Office in counterpart European application No. 15786541.1.

* cited by examiner

LIPOSOME COMPOSITION AND METHOD FOR PRODUCING SAME

CROSS-REFERENCE TO RELATED APPLICATIONS

The present application is a divisional of U.S. application Ser. No. 15/336,158, filed Oct. 27, 2016, which is a continuation of PCT/JP2015/062984 filed on Apr. 30, 2015, and claims priority under 35 U.S.C. § 119 of Japanese Patent Application No. 94141/2014 filed on Apr. 30, 2014. Each of these are incorporated herein by reference in its entirety.

BACKGROUND OF THE INVENTION

1. Field of the Invention

The present invention relates to a liposome composition and a method for producing the same. The present invention relates to a liposome composition which can be preferably used for pharmaceutical applications and a method for producing the same.

2. Description of the Related Art

A liposome (hereinafter, also referred to as lipid vesicle) is a closed vesicle formed of a lipid bilayer membrane using lipids, and has a water phase (inner water phase) within the space of the closed vesicle. Liposomes are usually present in a state of being dispersed in an aqueous solution (outer water phase) outside the closed vesicle.

Liposomes have been studied for a variety of applications such as immune sensors, artificial red blood cells, and carriers of drug delivery systems taking advantage of features such as barrier capacity, compound retention capacity, biocompatibility, the degree of freedom of setting the particle size, ready biodegradability, and surface-modifying properties. In carrier applications, liposomes can encapsulate water-soluble compounds, lipophilic low-molecular weight materials, polymers and a wide range of materials.

In the case where liposomes are used particularly as a carrier for a drug delivery system, it is necessary to make a particle size to be about 200 nm or less in terms of permeation through a biological membrane. Further, in a carrier for a drug delivery system, it is also necessary to have liposomes which form particles having a good dispersibility under the temperature conditions of about 37° C. which is the body temperature of a mammal. In particular, with regard to nano-sized fine particles, it is preferred to impart preservation stability from various viewpoints such as aggregation, precipitation, and leakage of drugs.

As a carrier for a drug delivery system, in the case where a drug (solution or the like containing liposomes containing a drug) is administered by intravenous injection, high safety is required for an intravenous injection product. Additives such as chlorinated solvents, for example chloroform, or a dispersant (hereinafter, the dispersant also includes a dispersing aid or the like) whose use are not allowed are undesirable. In addition, impartment of stability to a pharmaceutical product is also necessary, and correspondingly suppression of drug leakage, lipid decomposition or the like after storage is required. Further, suitability for sterile filtration is also required in order to guarantee sterility. When it is desired to produce liposomes as a pharmaceutical product on an industrial scale, it is necessary to take into account the requirements as described above.

In a drug delivery system, a liposome composition containing a pharmaceutical (drug) is required to deliver the pharmaceutical into an affected area and then release a required amount of the drug therein. However, achieving both easy release and preservation stability of a drug in a liposome composition is a contradictory problem. Therefore, there is a need for achieving both of them.

JP2013-022482A discloses a method for producing a liposome by an emulsification method without passing through a drying and solidifying step of a lipid membrane. Disclosed therein is a method for producing a liposome, using a water-soluble emulsifier which does not destroy a liposome lipid membrane, as an emulsifier, specifically Pluronic as a nonionic surfactant. Generally, surfactants significantly affect the strength of the liposome membrane, which will therefore require improving.

JP1994-009374A (JP-H06-009374A) discloses a liposome composition formed by encapsulating a drug-containing liquid 2.0 to 5.0-fold hyper-osmotic with respect to an osmotic pressure of a biological fluid of a warm-blooded animal, within a liposome which is a small unilamellar vesicle having a membrane phase transition temperature of 40° C. to 45° C. In addition, it is also disclosed that this liposome composition is a liposome composition obtained through a drying and solidifying step of the mixed lipid membrane. By rendering the conditions of the lipid membrane 2.0 to 5.0-fold hyper-osmotic with respect to an osmotic pressure of a biological fluid of a warm-blooded animal, this liposome composition has properties by which the release of a drug is suppressed at a low temperature and the drug is released all at once at a high temperature, for the purpose of hyperthermia. Because the release suppression at a low temperature has a short time duration of less than a few tens of minutes, and there is weakness in the lipid membrane that has undergone the drying and solidifying step of the mixed lipid membrane, no reference is made to preservation stability over an extended period of time or release control on the order of several tens of hours.

In all of the above-mentioned documents, a liposome composition having a practically required long-term preservation stability and also having a release rate of a drug on the order of several tells of hours and a method for producing the same have not been fully established, and correspondingly improvements are desired.

SUMMARY OF THE INVENTION

In a method of adsorbing and retaining a drug onto a lipid membrane of a liposome, release of the drug to the outside of the liposome becomes difficult due to strong interactions such as hydrophobic interactions and electrostatic interactions. Therefore, the configuration of the liposome composition after production can be maintained, whereby it is easy to secure long-term preservation stability.

In this case, it becomes difficult to release a drug to an affected area since interactions are too strong. Therefore, it is ideal to encapsulate a drug in a dissolved state in an inner water phase of a liposome, and also a liposome composition is rendered to have hyper-osmotic conditions, thus promoting release of the drug from the liposome composition, whereby it is possible to realize more suitable drug delivery. However, rendering to have hyper-osmotic conditions results in ready leakage of the drug from the liposome composition, so it is difficult to ensure long-term preservation stability.

Further, in the case where it is desired to effectively deliver a drug to an affected area, it is preferable that liposomes are fine particles having an average particle size of 100 nm or less. However, microparticulation contributes to an increase in the curvedness (curvature of a liposome membrane, thus resulting in difficulty of encapsulating a drug.

The present invention has been made in view of the foregoing circumstances, and an object of the present invention is to provide a liposome composition which has practically required long-term storability, and which has a release rate of a drug on the order of several tens of hours, and a method for producing the same.

As a result of extensive studies, the present inventors have discovered a liposome composition which has a high preservation stability while an appropriate release performance of a water-soluble drug is imparted due to rendering an inner water phase hyper-osmotic, and which also has a release rate of a drug on the order of several tens of hours, and a method for producing the same. The present invention has been completed based on this discovery. That is, according to the present invention, there is provided a liposome composition, comprising:

liposomes obtained from lipids dissolved and emulsified in an organic solvent, each of which has an inner water phase and an aqueous solution which constitutes an outer water phase and in which the liposomes are dispersed, wherein each of the liposomes encapsulates a water-soluble drug in a dissolved state, and an osmotic pressure of the inner water phase is 2-fold to 8-fold relative to the osmotic pressure of the outer water phase.

In the liposome composition of the present invention, the following aspects are preferred.

Preferably, the liposome has a single lamellar structure.

Preferably, an average particle size of the liposomes is 5 nm to 100 nm.

Preferably, the liposome contains at least hydrogenated soybean phosphatidylcholine, 1,2-distearoyl-3-phosphatidylethanolamine-polyethylene glycol, and cholesterol.

The present invention is a pharmaceutical composition comprising the above-described liposome composition.

The present invention is a method for producing a liposome composition, comprising:

an emulsifying step of emulsifying lipids dissolved in an organic solvent to form liposomes, without a drying and solidifying step;

a drug loading step of encapsulating a water-soluble drug in the liposomes obtained in the emulsifying step; and an osmotic pressure adjusting step of adjusting an osmotic pressure of an inner water phase of the liposome to 2-fold to 8-fold relative to the osmotic pressure of an outer water phase.

In the method for producing a liposome composition according to the present invention, the following aspects are preferred.

Preferably, the liposomes obtained after the emulsifying step are used in a next step without extrusion processing.

Preferably the drug loading step and the osmotic pressure adjusting step are carried out simultaneously.

According to the liposome composition of the present invention, it is possible to provide a liposome composition which encapsulates a water-soluble drug in a dissolved state, and also exhibits excellent preservation stability even in the stringent conditions with respect to preservation stability where an osmotic pressure of an inner water phase is 2-fold to 8-fold relative to the osmotic pressure of an outer water phase.

Further, according to another aspect of the liposome composition of the present invention, it is possible to provide a liposome composition in which the osmotic pressure of the inner water phase is 2-fold to 8-fold relative to the osmotic pressure of the outer water phase, and which encapsulates a water-soluble drug in a dissolved state and is also capable of achieving a release rate on the order of several tens of hours.

Further, according to the method for producing a liposome composition of the present invention, it is possible to provide a liposome composition having a good production suitability (for example, sterile filtration suitability, or the like), an average particle size of 100 nm or less, a uniform particle size distribution, and also an excellent preservation stability.

Further, according to another aspect of the method for producing a liposome composition of the present invention, it is possible to efficiently produce a liposome composition which is capable of achieving all of an average particle size and particle size distribution, production suitability (for example, sterile filtration suitability, or the like), and preservation stability required for a formulation, each of which is suitable for medicinal use, and which encapsulates a water-soluble drug in a dissolved state, on an industrial scale.

DESCRIPTION OF THE PREFERRED EMBODIMENTS

Figure 1:
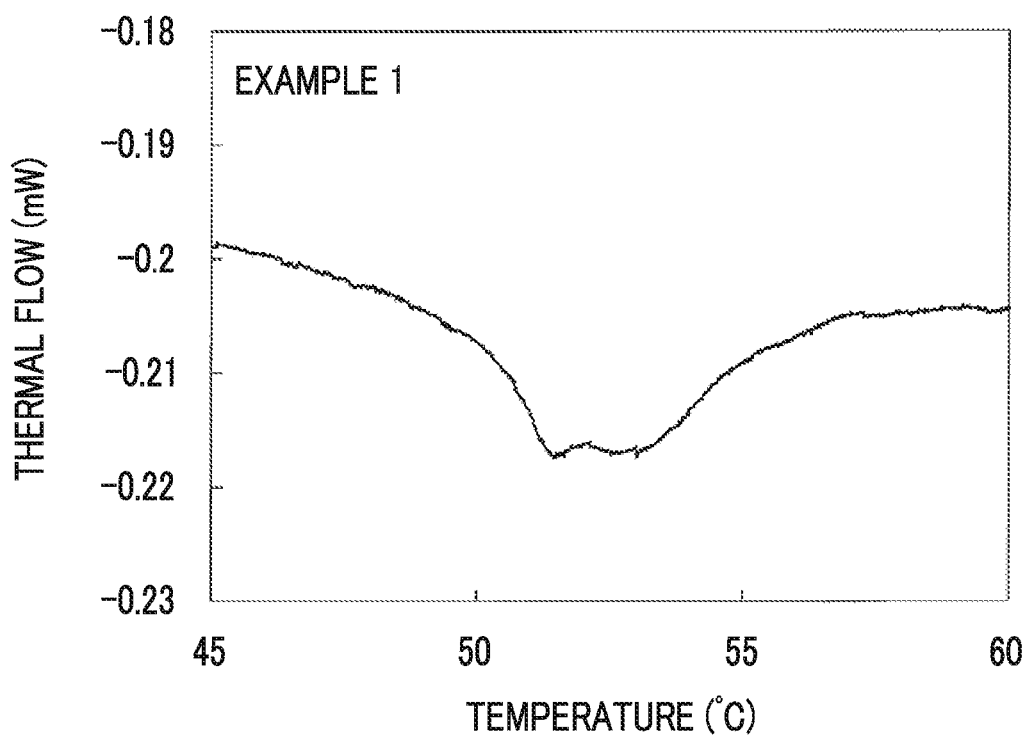
FIG. 1 is a DSC thermogram of liposomes produced by an emulsification method (Example 1).

The term "step" as used herein includes not only an independent step, but also a step which may not be clearly separated from another step, insofar as an expected effect of the step can be attained.

The numerical value ranges shown with "to" in the present specification means ranges including the numerical values indicated before and after "to" as the minimum and maximum values, respectively.

In the present invention, unless otherwise specified, % means mass percent.

In referring herein to a content of a component in a composition, in a case where plural substances exist corresponding to a component in the composition, the content means, unless otherwise specified, the total amount of the plural substances existing in the composition.

Hereinafter, the present invention will be described in detail.

The present invention is a liposome composition including liposomes obtained from lipids dissolved and emulsified in an organic solvent, each of which has an inner water phase and an aqueous solution which constitutes an outer water phase and in which the liposomes are dispersed, in which each of the liposomes encapsulates a water-soluble drug in a dissolved state, and the osmotic pressure of the inner water phase is 2-fold to 8-fold relative to the osmotic pressure of the outer water phase.

(Liposome)

The liposome is a closed vesicle formed of a lipid bilayer membrane using lipids, and has a water phase (inner water phase) within the space of the closed vesicle. The inner water phase contains water and the like. The liposome is usually present in a state of being dispersed in an aqueous solution (outer water phase) outside the closed vesicle. The liposome may be single lamellar (which is also referred to as monolayer lamellar or unilamellar, and is a structure having a single bilayer membrane) or multilayered lamellar (which is also referred to as multilamellar and is an onion-like structure having multiple bilayer membranes where individual layer's are compartmented by aqueous layers). In the present invention, a single lamellar liposome is preferred from the viewpoint of safety and stability in pharmaceutical applications.

The liposome is not particularly limited in terms of form as long as it is a liposome capable of encapsulating a drug. The "encapsulating" means taking a form where a drug is contained in an inner water phase with respect to the liposome. For example, the liposome may be a form where a drug is encapsulated within a closed space formed of a membrane, a form where a drug is included in the membrane itself, or a combination thereof.

The size (average particle size) of a liposome is not particularly limited, and it is 2 to 200 nm, preferably 5 to 150 nm, more preferably 5 to 120 nm, and still more preferably 5 to 100 nm. In the present invention, the "average particle size" means an average value of diameters of liposomes as measured by a light scattering method.

The liposome is preferably in the form of a spherical shape or a morphology close thereto.

The component (membrane component) constituting the lipid bilayer of a liposome is selected from lipids. As the lipid, any one may be used as long as it is dissolved in a mixed solvent of a water-soluble organic solvent and an ester-based organic solvent. Specific examples of lipids include phospholipids, lipids other than phospholipids, cholesterols and derivatives thereof. These components may be composed of single or plural components.

Examples of the phospholipid include natural or synthetic phospholipids such as phosphatidylcholine (lecithin), phosphatidyl glycerol, phosphatidic acid, phosphatidyl ethanolamine, phosphatidyl serine, phosphatidyl inositol, sphingomyelin, and cardiolipin, or hydrogenated products thereof (for example, hydrogenated soybean phosphatidylcholine (HSPC)). Among these, preferred is a hydrogenated phospholipid such as hydrogenated soybean phosphatidylcholine, or sphingomyelin, and more preferred is hydrogenated soybean phosphatidylcholine. In the present invention, the "phospholipid" also encompasses a phospholipid derivative in which the phospholipid is modified.

Lipids other than phospholipids may be lipids containing no phosphoric acid, and examples thereof include, but are not particularly limited to, glycerolipid which does not contain a phosphoric acid moiety in the molecule, and sphingolipid which does not contain a phosphoric acid moiety in the molecule. In the present invention, the term "lipids other than phospholipids" also encompasses derivatives of lipids other than phospholipids in which modifications have been made to lipids other than phospholipids.

In the case where the lipid other than phospholipid contains a basic functional group, for example, in the case where the lipid other than phospholipid is a material where a compound having a basic functional group is bonded to a lipid, the lipid is referred to as a cationized lipid. The cationized lipid, for example, becomes possible to modify the membrane of the liposome and therefore can enhance the adhesiveness to cells which are target sites.

Examples of the cholesterols include cholesterol. When the average particle size decreases to 100 nm or less, the curvature of the lipid membrane becomes higher. Since the deformation of the membrane arranged in the liposome also becomes larger, a water-soluble drug becomes more susceptible to leakage. However, as a means for suppressing leakage properties, it is effective to add cholesterol or the like in order to fill the deformation of the membrane caused by lipid.

In addition to the above-mentioned components, a hydrophilic polymer or the like for improving retentivity in blood, fatty acid, diacetyl phosphate or the like as a membrane structure stabilizer, or α-tocopherol or the like as an antioxidant may be added to the liposome. In the present invention, it is preferable not to use additives such as a dispersing aid not authorized for intravenous injection use in pharmaceutical applications, for example, a surfactant or the like.

The liposome of the present invention preferably contains hydrophilic polymer-modified products of phospholipids, lipids other than phospholipids, or cholesterols as phospholipids, lipids other than phospholipids, cholesterols and derivatives thereof.

Examples of the hydrophilic polymer include, but are not particularly limited to, polyethylene glycols, polyglycerols, polypropylene glycols, polyvinyl alcohols, a styrene-maleic anhydride alternating copolymer, polyvinylpyrrolidone, and synthetic polyamino acid. The above-mentioned hydrophilic polymers may be used alone or in combination of two or more thereof.

Among these, from the viewpoint of retentivity in blood of a formulation, preferred are polyethylene glycols, polyglycerols, or polypropylene glycols, and more preferred is polyethylene glycol (PEG), polyglycerol (PG), or polypropylene glycol (PPG). Polyethylene glycol (PEG) is most commonly used and is preferable due to having an effect of improving retentivity in blood.

The molecular weight of PEG is not particularly limited. The molecular weight of PEG is 500 to 10,000 daltons, preferably 1,000 to 7,000 daltons, and more preferably 2,000 to 5,000 daltons.

In the liposome of the present invention, it is preferable to use a lipid modified by PEG (PEG-modified lipid), together with the main lipid contained in the liposome. Examples of the PEG-modified lipid include 1,2-distearoyl-3-phosphatidylethanolamine-polyethylene glycol such as 1,2-distearoyl-3-phosphatidylethanolamine-PEG2000 (manufactured by Nippon Oil & Fats Co., Ltd.), 1,2-distearoyl-3-phosphatidylethanolamine-PEG5000 (manufactured by Nippon Oil & Fats Co., Ltd.) and distearoyl glycerol-PEG2000 (manufactured by Nippon Oil & Fats Co., Ltd.). These PEG-modified lipids may be added in an amount of 0.3 to 50 mass %, preferably 0.5 to 30 mass %, and more preferably 1 to 20 mass % with respect to total lipid content.

In the liposome of the present invention, preferred is a lipid combination of hydrogenated soybean phosphatidylcholine (a main lipid contained in liposome), 1,2-distearoyl-3-phosphatidylethanolamine-polyethylene glycol (a lipid used in combination with the main lipid), and cholesterol.

(Composition of Membrane of Liposome)

A phase transition temperature or Tm of an object to be measured can be measured in accordance with differential scanning calorimetry (DSC). The phase transition temperature or Tm refers to a temperature at which a lipid transits from a low-temperature gel phase characterized by ordered phospholipids in the lipid bilayer of liposome (solid-ordered phase) into a high-temperature fluid phase having high three-dimensional irregularities (liquid-disordered phase). Specifically, uniformity of the membrane composition of the resulting liposomes can be seen by the shape of a phase transition peak (endothermic peak derived from the breakdown of a lipid structure) on a DSC thermogram.

Differential seaming calorimetry can be carried out, for example, by using a differential scanning calorimeter. The differential scanning calorimeter is not particularly limited. For example, a DSC120 manufactured by Seiko Instruments Inc. (SII), or the like may be used. For a sample of liposomes, the rate of temperature increase is not particularly limited, but it may be 0.2° C./min to 20° C./min. In addition, there is no limitation to the scanning temperature range which may be a range at which a desired endothermic peak can be observed, depending on the phase transition temperature of liposomes. For example, it may be scanned from around 5° C. to around 100° C.

For example, FIG. 1 is a DSC thermogram for liposomes produced by an emulsification method of the present invention (Example 1) and liposomes produced by a Bangham method (Comparative Example 1). In liposomes having a high osmotic pressure of an inner water phase, a portion of the lipid membrane has been known to form an interdigitated gel phase ($L_\beta I$ phase), and endothermic peaks attributable to two components of interdigitated gel phase and lamellar gel phase ($L_\beta'$ phase) take place. Two clear endothermic peaks were obtained in the liposomes obtained in Example 1, whereas the endothermic peak was not separated into two peaks in the liposomes obtained in Comparative Example 1. This is because the latter has a non-uniform composition of a liposome membrane, so formation of an interdigitated gel phase does not occur uniformly for individual liposome particles, and liposome particles having various endothermic peaks are present to become apparently a single peak. On the other hand, two peaks are clearly shown in Example 1 of the present invention, and therefore it can be seen that the composition of the liposome membrane is uniform.

(Drug)

The liposome of the present invention may contain at least one of water-soluble drugs as a drug.

In the case of a water-soluble drug, a form to be retained in the inner water phase of the liposome is advantageous, but there may be a case where a drug becomes readily susceptible to leakage because the lipid bilayer membrane is thin and soft. However, according to the method for producing a liposome of the present invention, it is possible to produce a liposome having safety and stability even when the particle size of the liposome is set to about 100 nm or less.

The drug encompassed by the drug may be any water-soluble drug that can be encapsulated in liposomes, and specific examples thereof include, but are not limited to, water-soluble materials having a physiological activity or a pharmacological activity such as enzymes, proteins, peptides, nucleic acids (DNA, mRNA, siRNA, miRNA), low-molecular weight compounds, sugars (oligosaccharides and polysaccharides), polymer compounds, antitumor agents, antimicrobial agents, contrast agents, antioxidants, anti-inflammatory agents, whitening agents, humectants, and hair growing agent. In the case of using a liposome as a carrier for a drug delivery system, the water-soluble drug is preferably a low-molecular weight compound from the viewpoint of stability.

Specific examples of the water-soluble drug include anticancer agents such as an anthracycline-based anticancer agent such as doxorubicin, daunorubicin or epirubicin, a cisplatin-based anticancer agent such as cisplatin or oxaliplatin, a taxane-based anticancer agent such as paclitaxel or docetaxel, a vinca alkaloid-based anticancer agent such as vincristine or vinblastine, a bleomycin-based anticancer agent such as bleomycin, and a sirolimus-based anticancer agent such as sirolimus, and metabolic antagonists such as methotrexate, fluorouracil, gemcitabine, and cytarabine. Among these, preferred is a water-soluble drug such as doxorubicin, gemcitabine, or pemetrexed.

(Water-Soluble Drug Encapsulated in Dissolved State)

The water-soluble drug encapsulated in the liposome of the present invention is present in a dissolved state in the inner water phase of the liposome. Here, with regard to the dissolved state, it is deemed to have been encapsulated in a dissolved state in a case where the amount of the drug filled with respect to the volume of the liposome is below the saturation solubility of the drug in the composition liquid of the inner water phase. Further, even when the amount of the drug filled is above the saturation solubility of the drug, a case where drug crystals are not observed by Cryo-TEM and diffraction patterns attributable to crystal lattice are not observed by XRD measurement indicates that most of the drug is dissolved due to acceleration of dissolution by physicochemical environment created by the lipid membrane, partial incorporation of the drug into the lipid membrane or the like and is deemed to have been encapsulated in a dissolved state. Further, a case which is encapsulated by a loading method of encapsulating a drug via the formation of a solid inside the liposome is not the dissolved state referred to in the present invention, even when the drug is a highly water-soluble drug.

The water-soluble drug to be encapsulated in a dissolved state preferably has a solubility in water of 1 mg/ml or more, and more preferably a solubility in water of 10 mg/ml or more.

(Method for Producing Liposome Composition)

The method for producing a liposome according to the present invention is a method for producing a liposome composition including:

an emulsifying step of emulsifying lipids dissolved in an organic solvent to form a liposome, without a drying and solidifying step;

a drug loading step of encapsulating a water-soluble drug in the liposome obtained in the emulsifying step; and a remote loading step of adjusting an osmotic pressure of an inner water phase of the liposome to 2-fold to 8-fold relative to the osmotic pressure of an outer water phase.

The method for producing a liposome composition may include, if desired, other steps such as an evaporating step of evaporating the organic solvent used in the emulsifying step.

The emulsifying step of emulsifying a mixed lipid dissolved in an organic solvent to form a liposome, without a drying and solidifying step, is not limited as long as it is a step of emulsification, but it is preferably a step of applying a high shearing force and performing microparticulation with an emulsifying step including an organic solvent. If necessary, evaporation (desolvation) of the organic solvent used in the emulsifying step may be carried out to form a liposome.

(Emulsifying Step)

In the emulsifying step, an oil phase where at least one lipid has been dissolved in an organic solvent and a water phase are mixed to prepare an aqueous solution containing lipids, which is then emulsified with stirring. An oil phase where lipid have been dissolved in an organic solvent and a water phase are mixed, stirred and emulsified to thereby prepare an emulsion where an oil phase and a water phase are emulsified in an O/W type. After mixing, a liposome is formed by removing a portion or all of the organic solvent derived from the oil phase using an evaporating step to be described below. Alternatively, a portion or all of the organic solvent in the oil phase is evaporated in the course of the stirring-emulsification to form a liposome.

As a method of stirring, ultrasonic waves or mechanical shearing force is used for particle miniaturization. In addition, extruder processing of allowing to pass through a filter having a certain pore diameter or microfluidizer processing may be carried out for uniformity of particle sizes. Use of an extruder or the like can result in decomposition of secondarily formed multivesicular liposomes into univesicular liposomes. In the present invention, it is preferred from the viewpoint of simplification of the production process that a liposome in a state of a drug being not loaded is used in the next step without extrusion processing.

In the present invention, an average particle size of a liposome to be prepared can be controlled by arbitrarily selecting the speed and time of stirring. In view of obtaining a liposome having safety and stability, it is preferable to provide shearing at a circumferential speed of 20 m/sec or higher to an aqueous solution containing lipid. The shearing is not limited, and a specific example thereof is preferably shearing at a circumferential speed of 20 m/sec to 35 m/sec, and more preferably shearing at a circumferential speed of 23 m/sec to 30 m/sec.

(Oil Phase)

As the organic solvent serving as an oil phase, a mixed solvent of a water-soluble organic solvent and an ester-based organic solvent is used. In the present invention, it is preferred that an organic solvent such as chloroform, methylene chloride, hexane, or cyclohexane is not substantially used as the organic solvent, and it is more preferred that these organic solvents are not used at all.

The water-soluble organic solvent is not particularly limited, and it is preferably an organic solvent having a property that is optionally miscible with water. Specific examples of the water-soluble organic solvent include alcohols such as methanol, ethanol, n-propanol, isopropanol, n-butanol, isobutanol, and t-butanol; glycols such as glycerol, ethylene glycol, and propylene glycol; and polyalkylene glycols such as polyethylene glycol. Among these, preferred are alcohols. The alcohol is preferably at least one selected from ethanol, methanol, 2-propanol, or t-butanol, more preferably at least one selected from ethanol, 2-propanol, or t-butanol, and still more preferably ethanol.

The ester-based organic solvent is not particularly limited, and it is preferably an ester obtained from the reaction of organic acids and alcohols. Specifically, the ester-based organic solvent is preferably at least one selected from ethyl acetate, methyl acetate, isopropyl acetate, t-butyl acetate, or methyl propionate, more preferably ethyl acetate, isopropyl acetate, or methyl propionate, and still more preferably ethyl acetate.

The mixing ratio of water-soluble organic solvent:ester-based organic solvent is not particularly limited, and it may be 90:10 to 30:70, preferably 80:20 to 40:60, and more preferably 80:20 to 70:30 by mass ratio. The mixed solvent of a water-soluble organic solvent and an ester-based organic solvent may further contain an aqueous solvent to be described below, such as water or buffer. The aqueous solvent may be added in a range of, for example, 1 to 30 mass %. The pH of the mixed solvent is not particularly limited, and it is preferably in the range of about 3 to 10, and more preferably about 4 to 9. The ester-based organic solvents may contain physiologically active substances or the like such as various medicines which are soluble in these solvents.

In the case where ethanol is used as the water-soluble organic solvent and ethyl acetate is used as the ester-based organic solvent, the mixing ratio of ethanol:ethyl acetate is not particularly limited, and it is preferably 80:20 to 70:30 by a mass ratio.

The concentration of the lipid is not particularly limited and may be appropriately adjust, but it may be 40 g/L to 250 g/L, preferably 40 g/L to 200 g/L in terms of a solution where a mixed solution of a water-soluble organic solvent and an ester-based organic solvent serves as a solvent.

(Water Phase)

The water phase means an outer water phase and an inner water phase.

The outer water phase as used herein means an aqueous solution in which the liposomes are dispersed. For example, in the case of an injection, a solution occupying the outside of the liposome of a dispersion liquid of liposomes packaged and stored in a vial or prefilled syringe becomes an outer water phase. Also, similarly for a liquid to be dispersed at the time of use when administered by means of an attached dispersion solution or other solutions, a solution occupying the outside of the liposome of a dispersion liquid of liposomes becomes an outer water phase.

The inner water phase as used herein means a water phase in the closed vesicle with a lipid bilayer membrane therebetween.

As a liposome-dispersing aqueous solution (outer water phase) when producing liposomes, water (distilled water, water for injection, or the like), physiological saline, various buffers, an aqueous solution of sugars or a mixture thereof (aqueous solvent) is preferably used. The buffer is not limited to organic and inorganic buffer solutions, and a buffer having a buffering action in the vicinity of a pH close to that of the body fluid is preferably used and examples thereof include phosphate buffer, tris buffer, citrate buffer, acetate buffer, and Good's buffer. The pH of the water phase is not particularly limited, and it may be 5 to 9, preferably 7 to 8. For example, a phosphate buffer (for example, pH=7.4) is preferably used. The inner water phase of the liposome may be a liposome-dispersing aqueous solution when producing liposomes, or may be water, physiological saline, various buffers, an aqueous solution of sugars or a mixture thereof which are newly added. The water used as an outer water phase or an inner water phase is preferably free from impurities (dust, chemicals, or the like).

The physiological saline refers to an inorganic salt solution adjusted to be isotonic with the human body fluid, and may further have a buffering function. Examples of the physiological saline include saline containing 0.9 w/v % of sodium chloride, phosphate buffered saline (hereinafter, also referred to as PBS), and tris buffered saline.

(Evaporating Step)

In the present invention, an evaporating step may be provided if necessary. In the evaporating step, an organic solvent is evaporated from the aqueous solution containing the liposomes obtained in the emulsifying step. In the present invention, the evaporating step includes at least one of a step of forcibly removing a portion or all of the organic solvent derived from the oil phase as an evaporating step, and a step of naturally evaporating a portion or all of the organic solvent in the oil phase during the course of stirring-emulsification.

The method of evaporating an organic solvent in the evaporating step is not particularly limited. For example, at least one of a step of heating to evaporate an organic solvent, a step of continuing the standing or slow stirring after emulsification, or a step of performing vacuum degassing may be carried out.

In the present invention, in the step of evaporating an organic solvent, it is preferred that the concentration of an organic solvent contained in an aqueous solution containing liposomes is to be 15 mass % or less within 30 minutes from after the start of a step of evaporating the organic solvent.

A liquid temperature when carrying out the production method of the present invention can be appropriately adjusted, but the liquid temperature at the time of mixing an oil phase and a water phase is preferably higher than or equal to a phase transition temperature of the lipid to be used. For example, in the case where a lipid having a phase transition temperature of 35° C. to 40° C. is used, the liquid temperature is preferably set to 35° C. to 70° C.

The aqueous solution containing the liposomes prepared via an emulsifying step may be subjected to post-processing such as centrifugation, ultrafiltration, dialysis, gel filtration, or freeze-drying, for removal of components that had not been included in the liposomes, or adjustment of a concentration and an osmotic pressure.

Particle sizes of the resulting liposomes can be made uniform by using dialysis, filtration, extrusion processing, or the like. In the method for producing a liposome composition according to the present invention, it is preferred to prepare empty liposomes in a state where a drug is not loaded, without subjecting to extrusion processing. Moreover, if it is desired to separate the drug encapsulated in liposomes from the drug not encapsulated in liposomes, centrifugation, dialysis, gel filtration, or the like may be employed.

(Extrusion Processing)

Extrusion processing means a step of passing liposomes through a filter having a fine pore to apply a physical shear force, thereby performing microparticulation. When the liposomes are passed through, rapid microparticulation may be achieved by incubating the liposome dispersion liquid and the filter at a temperature higher than or equal to the phase transition temperature of the membrane constituting the liposome.

(Drug Loading Step)

In the drug loading step of the present invention, in the case of encapsulating a water-soluble drug in liposomes, the drug can be encapsulated in the inner water phase of the liposome by a method of dissolving the drug in an aqueous medium capable of performing hydration and swelling, followed by heating at a temperature higher than or equal to the phase transition temperature, and sonication or extrusion. A drug may also be encapsulated in an inner water phase by dissolving the drug in the water phase at a time of lipid emulsification.

(Osmotic Pressure Adjusting Step)

In the present invention, it becomes easy to release a drug by rendering the inner water phase of the liposomes hyper-osmotic (pressure difference with an outer water phase) through an osmotic pressure adjusting step. The release rate can be controlled by setting the osmotic pressure. The osmotic pressure adjusting step is not particularly limited, and a method such as dialysis after the drug loading step may be employed. This makes it possible to adjust the osmotic pressure. In the present invention, it is preferable to carry out the drug loading step and the osmotic pressure adjusting step (preferably adjusting of the osmotic pressure of an inner water phase) at the same time, from the viewpoint of production efficiency.

In the present invention, by controlling the release, for example, in the case of using the liposome of the present invention as a drug delivery system, it is possible to release the required amount of the drug that is needed in an affected area to be targeted. However, a hyper-osmotic liposome is easy to release a drug, but becomes easy to leak a drug during storage, so it is difficult to achieve both good releseability and preservation stability. According to the liposome composition of the present invention, it has an unexpected effect capable of achieving both easy release and preservation stability of a drug by setting the osmotic pressure of the inner water phase to 2-fold to 8-fold relative to the osmotic pressure of outer water phase, for liposomes having an inner water phase obtained from the emulsified lipids.

In general, as a method for rendering an inner water phase hyper-osmotic, for example, there is a method of making an inner water phase and an outer water phase of a liposome in which a drug has not encapsulated to have a high osmotic pressure, and then lowering the osmotic pressure of the outer water phase by dialysis or the like. In that case, in a subsequent drug loading step to be performed, there may be a case where the drug contained in the inner water phase is leaked, and also the osmotic pressure of the inner water phase is decreased.

Therefore, in the present invention, along with loading of a drug, an inner water phase is replaced with a solution of a high osmotic pressure, and then removal of the drug in an outer water phase and lowering of the outer water phase osmotic pressure are carried out simultaneously by dialysis, whereby it is possible to obtain a liposome composition capable of achieving both easy release and preservation stability of a drug.

In the liposome of the present invention, the osmotic pressure of the inner water phase is 2-fold to 8-fold, preferably 2.5-fold to 6-fold, more preferably 3-fold to 5-fold, with respect to the osmotic pressure of the outer water phase. By setting to be 2-fold or higher-fold, the lipid bilayer membrane of the liposome is generally known to show a structure such as a double membrane structure or an interdigitated structure. When the osmotic pressure of the inner water phase is 2-fold or higher-fold with respect to the outer water phase, the liposome begins to change from a double membrane structure into an interdigitated structure. In the present invention, in order to take a suitable interdigitated structure, it is preferable to control the osmotic pressure of the inner water phase by adjusting a cholesterol proportion, although the conditions for various lipids may be set up. As a result, it is possible to obtain a liposome composition capable of achieving both easy release and preservation stability of a drug.

In the liquid obtained after the final drug loading step, solutes of outer water phase and the inner water phase are homogenized, and the osmotic pressure at that time can be defined as an osmotic pressure of an inner water phase of the liposome composition to be completed. However, in a subsequent replacement-osmotic pressure adjusting step by dialysis of the outer water phase, a heating operation is limited only to a case where the solutes of inner water phase are sufficiently retained, such as being suppressed below phase transition of a lipid. In addition, the osmotic pressure of the outer water phase can be defined as an osmotic pressure of a dialysis liquid used in the final dialysis step. However, this is limited only to a case where the outer water phase was sufficiently replaced with a dialysis liquid. Further, for the finished solution of a liposome composition, it is also possible to obtain the osmotic pressure of the inner water phase and the outer water phase by quantifying the composition concentration of the solute in the outer water phase and the composition concentration of the solute in the inner water phase using centrifugation or ultrafiltration, and measuring the osmotic pressure of the composition liquid.

Measurement of an osmotic pressure may be carried out according to an osmolality measurement method described in the sixteenth revised Japanese Pharmacopoeia. Specifically, it is possible to determine osmolality by measuring the degree of freezing point (ice point) depression of water, in addition, the degree of freezing point depression of water is defined in terms of solute molar concentration, and it is also possible to determine osmolality from the solute molar concentration.

The outer water phase in the present invention is an aqueous solution which occupies the outside of liposomes. For example, in the case of an injection, a solution occupying the outside of liposomes of a dispersion liquid of the liposomes packaged and stored in a vial or prefilled syringe becomes an outer water phase. Also, similarly for a liquid to be dispersed at the time of use when administered by means of the appended dispersing solution or the other solution, a solution occupying the outside of liposomes becomes an outer water phase.

The osmotic pressure of the outer water phase in the present invention has a significant effect on the living body upon administration. In the case where the osmotic pressure of the outer water phase is far away from the osmotic pressure of a body fluid, hemolysis or pain caused by the movement of moisture in individual tissues occurs. Therefore, the osmotic pressure of the outer water phase in the present invention is preferably 200 to 400 mOsmol/L, more preferably 250 to 350 mOsmol/L, and most preferably isotonic with the body fluid.

(Sterile Filtration)

In order to formulate an aqueous solution containing liposomes, obtained by the method for producing a liposome composition according to the present invention, into a pharmaceutical composition, it is preferable to carry out sterile filtration. Regarding the filtration method, it is possible to remove unwanted materials from the aqueous solution containing liposomes by using a hollow fiber membrane, a reverse osmosis membrane, a membrane filter or the like. In the present invention, the aqueous solution containing liposomes is preferably filtered using a filter having a sterile pore size (preferably 0.2 μm sterile filter) although there is no particular limitation. Normally, adsorption or aggregation of liposomes onto a sterile filter may occur in the filtration step. However, the present invention has unexpected effects such as little influence of pressure loss or the like when performing filtration, since liposomes having a specific average particle size and uniform particle size distribution are obtained.

To prevent an effect of liposome deformation on the average particle size, the sterile filtration step and the below-described aseptic filling step are preferably carried out at a temperature lower than or equal to the phase transition temperature of the lipids constituting the liposome. For example, in the ease where the phase transition temperature of the lipid is around 50° C., the sterile filtration step and the below-described aseptic filling step are carried out at temperature of preferably about 0° C. to 40° C., and more specifically about 5° C. to 30° C.

(Aseptic Filling)

The aqueous solution containing the liposomes obtained after sterile filtration is preferably aseptically filled for medical applications. Known methods can be applied for aseptic filling. A liposome composition suitable for medical applications can be prepared by aseptically filling the liposome-containing aqueous solution in a container.

An aqueous solvent, an additive, or the like may be appropriately added to the aqueous solution containing the liposomes obtained by the present invention to thereby prepare a pharmaceutical composition containing a liposome composition. In connection with the route of administration, the pharmaceutical composition may also contain at least one of a tonicity agent, a stabilizer, an antioxidant, or a pH adjusting agent which is pharmaceutically acceptable.

The tonicity agent is not particularly limited and examples thereof include inorganic salts such as sodium chloride, potassium chloride, sodium hydrogen phosphate, sodium dihydrogen phosphate, and potassium dihydrogen phosphate; polyols such as glycerol, mannitol, and sorbitol; and sugars such as glucose, fructose, lactose, and sucrose.

The stabilizer is not particularly limited and examples thereof include sugars such as glycerol, mannitol, sorbitol, lactose, and sucrose.

The antioxidant is not particularly limited and examples thereof include ascorbic acid, uric acid, tocopherol homologues (for example, vitamin E, four tocopherol isomers $\alpha$, $\beta$, $\gamma$, and $\delta$), cysteine, and EDTA. Stabilizers and antioxidants may be respectively used alone or in combination of two or more thereof.

Examples of the adjusting agent include sodium hydroxide, citric acid, acetic acid, triethanolamine, sodium hydrogen phosphate, sodium dihydrogen phosphate, and potassium dihydrogen phosphate.

The pharmaceutical composition of the present invention may contain an organic solvent, collagen, polyvinyl alcohol, polyvinyl pyrrolidone, a carboxyvinyl polymer, sodium carboxymethyl cellulose, sodium polyacrylate, sodium alginate, water-soluble dextran, sodium carboxymethyl starch, pectin, methyl cellulose, ethyl cellulose, xanthan gum, gum arabic, casein, gelatin, agar, diglycerol, propylene glycol, polyethylene glycol, vaseline, paraffin, stearyl alcohol, stearic acid, human serum albumin (FISA), mannitol, sorbitol, lactose, PBS, sodium chloride, sugars, a biodegradable polymer, a serum-free medium, each of which is pharmaceutically acceptable, or an additive which is acceptable as a pharmaceutical additive.

In particular, in the context of the present invention, the pharmaceutical composition preferably contains ammonium sulfate, L-histidine, purified sucrose, sodium hydroxide, hydrochloric acid, or the like.

The container in which a pharmaceutical composition is filled is not particularly limited, and it is preferably made of a material having low oxygen permeability. Examples of the container include a plastic container, a glass container, and a bag made of a laminate film having an aluminum foil, an aluminum-deposited film, an aluminum oxide-deposited film, a silicon oxide-deposited film, a polyvinyl alcohol, an ethylene-vinyl alcohol copolymer, polyethylene terephthalate, polyethylene naphthalate, polyvinylidene chloride, or the like as a gas barrier layer. If necessary, light may be shielded by adopting a bag or the like using a colored glass, an aluminum foil, aluminum-deposited film or the like.

In the container in which a pharmaceutical composition is filled, in order to prevent oxidation by oxygen present in the space in the container, it is preferable to replace gases in the container space and drug solution with inert gases such as nitrogen. For example, an injection solution is bubbled with nitrogen, whereby the filling of the injection solution into a container can be carried out under a nitrogen atmosphere.

The administration method of a pharmaceutical composition is preferably parenteral administration. For example, intravenous injection such as intravenous drip, intramuscular injection, intraperitoneal injection, subcutaneous injection, or intrathecal injection may be selected. The specific administration method of a liposome composition includes, for example, a syringe, and administration by intravenous drip.

The dose of a drug contained in the pharmaceutical composition is usually selected in the range of 0.01 mg to 100 mg/kg body weight/day. However, the liposome composition of the present invention is not limited to such a dose.

INDUSTRIAL APPLICABILITY

According to the liposome composition and the method for producing the same of the present invention, it is possible to provide a liposome composition which is capable of achieving both easy release and preservation stability of a drug. The liposome composition of the present invention is applicable for pharmaceuticals, cosmetics, foodstuff, or the like, and is particularly useful for pharmaceutical applications.

EXAMPLES

Hereinafter, the present invention will be described in detail with reference to Examples. However, the present invention is not limited to such Examples.

The mixing ratio in the solvent composition refers to a volume ratio. For example, "ethanol/ethyl acetate=90/10" refers to 90% ethanol/10% ethyl acetate by a volume ratio.

Example 1 a) Preparation of Oil Phase 16.6 g of hydrogenated soybean phosphatidylcholine, 2.0 g of cholesterol and 4.3 g of N-(carbonyl-methoxypolyethylene glycol 2000)-1,2-distearoyl-sn-glycero-3-phosphoethanolamine sodium salt (hereinafter, also referred to as DSPE-PEG) were taken to be a molar ratio of 76/19/5, and then 405 mL of an organic solvent (ethanol/ethyl acetate=3/1) was added thereto, followed by warming to 70° C. and dissolving the lipids to prepare an oil phase.

b) Preparation of Water Phase 6 mM phosphate buffer (pH 7.86) was prepared to serve as a water phase.

c) Preparation of Drug-Unencapsulated Liposome

The water phase was warmed to 70° C., the oil phase was added in such a way that a volume ratio of water phase/oil phase=8/3 is achieved, and then two phases were mixed using a rotary agitation type emulsification machine at circumferential speed of 20 m/s and 13000 rpm for 30 minutes. Thereafter, the organic solvent and water were evaporated by blowing with nitrogen while warming to a temperature higher than or equal to the phase transition temperature, thereby concentrating the mixture to an about $\frac{1}{10}$ volume relative to the volume before emulsification, thus obtaining a drug-unencapsulated liposome. The particle size at this time was 66.9 nm.

d) Preparation of Drug-Encapsulated Liposome

Drag Loading 81.63 g of sodium chloride. 29.01 g of disodium hydrogen phosphate 12 hydrate, and 2.29 g of sodium dihydrogen phosphate dihydrate were dissolved in 948 g of water for injection to prepare PBS. 29.57 g of gemcitabine hydrochloride, 123.09 g. of PBS, 172.59 g of Japanese Pharmacopoeia water for injection, and 6.17 mL of 8M sodium hydroxide were mixed to prepare a drug solution. Subsequently, 137.2 mL of the drug solution, 140.0 mL of drug-unencapsulated liposomes, and 2.8 mL of 8M sodium hydroxide were mixed in each of two containers. The osmotic pressure of this liquid is 1039 mOsm/L which becomes the osmotic pressure of an inner water phase of the liposome composition to be completed. Then, this liquid was heated at 70° C. for 10 minutes, cooled to 40° C., and then diluted with a 1018 mM sucrose/37 mM histidine solution. After dilution, the liquid was pooled and used as a drug-loading liquid.

Completion of Liposome Composition by Dialysis

A 275 mM sucrose/10 mM histidine aqueous solution was prepared as a dialysis liquid. The osmotic pressure calculated from the solute molar concentration of this liquid was 285 mOsm/L. Using this dialysis liquid, dialysis was carried out at room temperature to remove unencapsulated gemcitabine hydrochloride and individual solutes present in the outer water phase of the drug-loading liquid, and the outer water phase was replaced with the dialysis liquid. From the above-described steps, a drug-encapsulated liposome composition having a gemcitabine hydrochloride concentration of 0.71 mg/mL, a particle size of 75.7 nm, an inner water phase osmotic pressure of 1039 mOsm/L, and an outer water phase osmotic pressure of 285 mOsm/L, with the osmotic pressure of the inner water phase being 3.6-fold relative to that of the outer water phase was obtained.

(Comparative Example 1) Preparation of Drug-Encapsulated Liposome According to Bandiam Method a) Preparation of Lipid Thin Film 1660 mg of hydrogenated soybean phosphatidylcholine, 431 mg of cholesterol and 205 mg of DSPE-PEG were taken in a molar ratio of 76/19/5 in a eggplant type flask, and then 20 mL of an organic solvent (chloroform/methanol=5/1) was added and dissolved therein. Subsequently, the organic solvent was removed in an evaporator, and a lipid thin film was obtained on the inner wall of the eggplant type flask.

b) Preparation of Water Phase 6 mM phosphate buffer (pH 7.86) was prepared to serve as a water phase.

c) Preparation of Drug-Unencapsulated Liposome 20 mL of a water phase was added to the eggplant type flask in which a lipid thin film was formed, and the lipid thin film was hydrated at 60° C. Then, the eggplant type flask was immersed in an ultrasonic cleaner to disperse the lipid thin film, thereby obtaining a coarse drug-unencapsulated liposome liquid. Sizing was carried out by sequentially passing the resulting liposome liquid through a 0.2 μm filter and a 0.05 μm filter using an extruder (Mini Extruder, manufactured by Avanti Polar Lipids), thereby preparing a drug-encapsulated liposomes. The resulting drug-encapsulated liposomes had a particle size of 83.2 nm.

d) Preparation of Drug-Encapsulated Liposome

Drug Loading 1.1 g of gemcitabine hydrochloride, 4.6 g of PBS prepared in d) of Example 1, 6.5 g of Japanese Pharmacopoeia water for injection, and 0.2 mL of 8M sodium hydroxide were mixed to prepare a drug solution. Subsequently, 12.12 g of the drug-unencapsulated liposomes and 0.2 mL of 8M sodium hydroxide were mixed into the drug solution. Next, this liquid was heated at 70° C. for 10 minutes and then cooled to 40° C. The osmotic pressure calculated from the solute molar concentration of this liquid is 1039 mOsm/L which becomes an inner water phase osmotic pressure of the liposome composition liquid to be completed. Subsequently, PBS prepared in d) of Example 1 was diluted 2.7-fold (by weight), and the drug solution was diluted 3-fold.

Completion of Liposome Composition by Dialysis

A 275 mM sucrose/10 mM histidine aqueous solution was prepared as a dialysis liquid. The osmotic pressure calculated from the solute molar concentration of this liquid was 285 mOsm/L. Using this dialysis liquid, dialysis was carried out at room temperature to remove unencapsulated gemcitabine hydrochloride and individual solutes present in the outer water phase of the drug-loading liquid, and the outer water phase was replaced with the dialysis liquid. From the above-described steps, a drug-encapsulated liposome composition having a gemcitabine concentration of 1.02 mg/mL, a particle size of 89.6 nm, an inner water phase osmotic pressure of 1039 mOsm/L, and an outer water phase osmotic pressure of 285 mOsm/L, with the osmotic pressure of the inner water phase being 3.6-fold relative to that of the outer water phase was obtained.

DSC Thermogram

Figure 2:
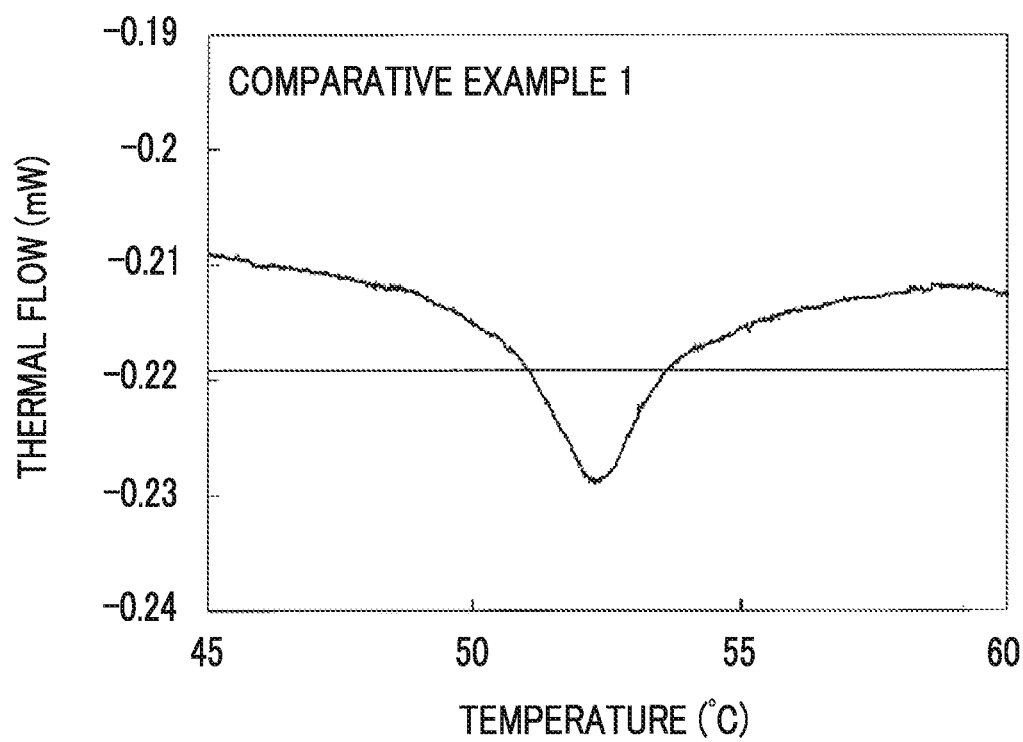
FIG. 2 is a DSC thermogram of liposomes produced by a Bangham method (Comparative Example 1).

FIG. 1 shows a DSC thermogram of liposomes (Comparative Example 1) prepared from liposomes (Example 1) produced by an emulsification method, FIG. 2 shows a DSC thermogram of liposomes (Comparative Example 1) produced by a Bangham method. 20 µL of a drug-encapsulated liposome liquid was filled and sealed in an aluminum hermetic pan (manufactured by Tzero), and measurements were carried out in a DSC Q2000 (manufactured by TA Instrument) at a scan rate of 0.5° C./minute from 25° C. to 70° C. Liposome Example 1 produced by an emulsification method of the present invention showed two clear peaks, a peak indicating an interdigitated gel phase and a peak indicating a lamellar gel phase. From this, it can be seen that the composition of the liposome membrane is uniform.

Example 2

A liposome composition was prepared in the same manner as in Example 1, except that, in the preparation of an oil phase, 49.9 g of hydrogenated soybean phosphatidylcholine, 6.1 g of cholesterol and 12.9 g of DSPE-PEG were used, and a water phase/oil phase mixed liquid was mixed using a rotary agitation type emulsification machine at a circumferential speed of 19 m/s and 12000 rpm for 30 minutes, and in the drug loading step, 10×PBS (manufactured by NIPPON GENE CO., LTD.) was used in place of PBS prepared in d) of Example 1, and 10×PBS (manufactured by NIPPON GENE CO., LTD.) was used in place of 2.7-fold diluted (by weight) PBS prepared in d) of Example 1, whereby a drug-encapsulated liposome composition having a gemcitabine concentration of 0.72 mg/mL, a particle size of 84 nm, a drug unencapsulation rate of 2.1%, an inner water phase osmotic pressure of 1039 mOsm/kg, and an outer water phase osmotic pressure of 285 mOsm/kg, with the osmotic pressure of the inner water phase being 3.6-fold relative to that of the outer water phase was obtained.

Measurement of Preservation Stability

The drug-encapsulated Liposomes of Example 2 were filled in a 2 mL vial and stored at 5° C. At a certain point of time, a sample was partially sampled. Using this sample, various evaluations given below were carried out, and the stability of the liposome composition according to the present invention was measured.

Measurement of Stability of Drug

Figure 3:
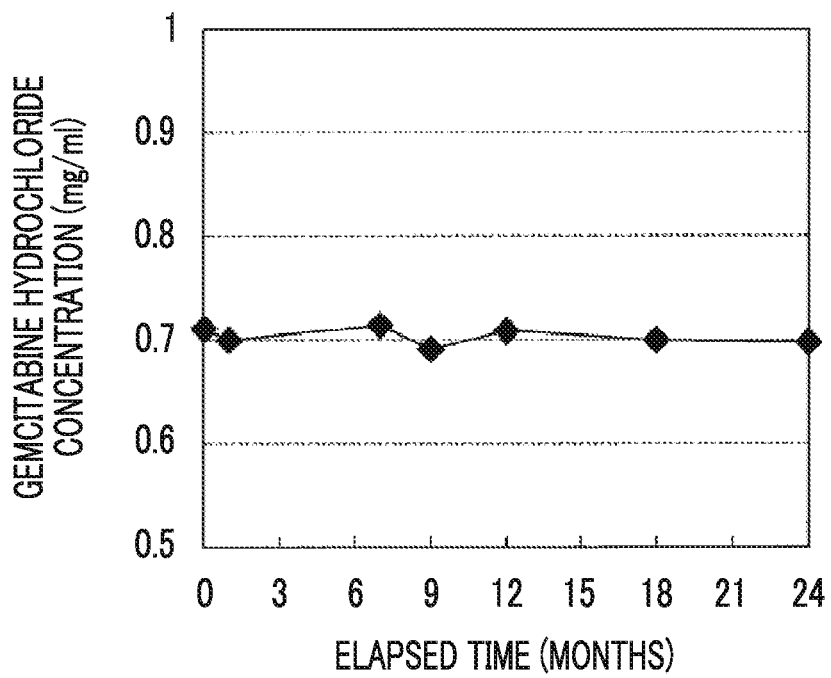
FIG. 3 is a plot of a relationship between an amount of drug encapsulated in the liposome and an elapsed time.

50 µL of the sampled sample was diluted 20-fold (by volume) with methanol to extract the drug encapsulated in a liposome. Subsequently, the extract was diluted 10-fold (by volume) with water, and the amount of drug contained in this liquid was quantified by HPLC. The results are shown in FIG. 3. Over an extended period of 12 months, the drug in the liposome composition of the present invention was found to be sufficiently stable.

Measurement of Unencapsulation Rate

Figure 4:
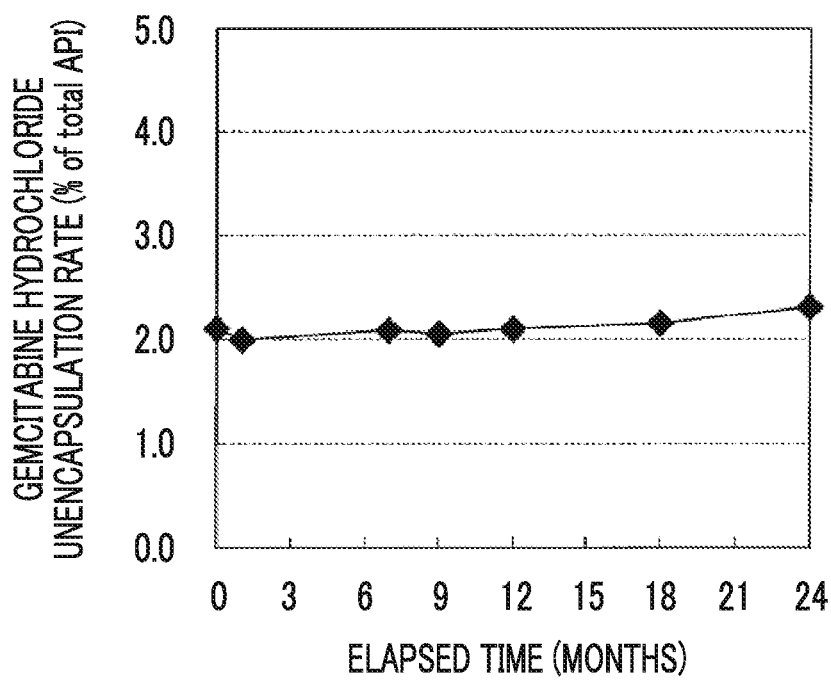
FIG. 4 is a plot of a relationship between an abundance ratio (unencapsulation rate) of a drug present in an outer water phase and the elapsed time.

50 µL of the sampled sample was diluted 10-fold (by volume) with water, and subjected to centrifugal filtration using an ultrafiltration filter (Amicon Ultra-0.5 10 kDa manufactured by Millipore Corporation) under the conditions of 7400×g, 30 minutes and 4° C. The amount of drug contained in the recovered filtrate was quantified by HPLC, and the abundance ratio (unencapsulation rate) of the drug present in the outer water phase was calculated by the following equation. The results are shown in FIG. 4.

$$\text{Unencapsulation rate (\%)} = (\text{drug concentration in filtrate} \times 10)/\text{drug concentration in formulation} \times 100 \quad \text{Equation:}$$

Surprisingly, since there was almost no change in the unencapsulation rate over an extended period of 12 months, the drug in the liposome composition of the present invention was found to be sufficiently stable without leaking into the outer water phase.

Measurement of Average Particle Size

Figure 5:
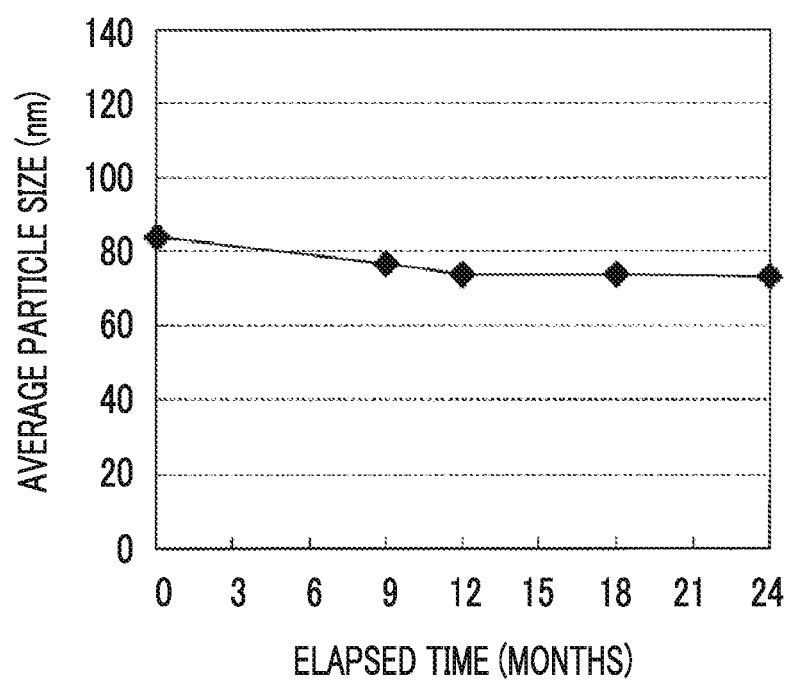
FIG. 5 is a plot of a relationship between a volume average particle size and the elapsed time.

The sampled sample was diluted 33-fold (by volume) with 1×PBS (manufactured by Gibco, Life Technology), and the volume average particle size was measured by a dynamic light scattering method using a FPAR-1000AS (manufactured by Otsuka Electronics Co., Ltd.). The results are shown in FIG. 5.

Since there was almost no change in the particle size over an extended period of 24 months, particles of the liposome composition of the present invention were found to be sufficiently stable.

Measurement of Drug Release Rate in Blood Plasma

50 µL of the sampled sample was diluted 20-fold with the mouse blood plasma, and incubated at 37° C. for 24 hours. Then, centrifugal filtration was carried out using an ultrafiltration filter (Amicon Ultra-0.5 10 kDa manufactured by Millipore Corporation) under the conditions of 7400×g, 30 minutes, and 4° C. The amount of drug contained in the recovered filtrate was quantified by HPLC, and the release rate of the drug released into blood plasma was calculated by the following equation.

$$\text{Drug release rate (\%)} = (\text{drug concentration in filtrate} \times 20)/\text{drug concentration in formulation} \times 100 \quad \text{Equation:}$$

Figure 6:
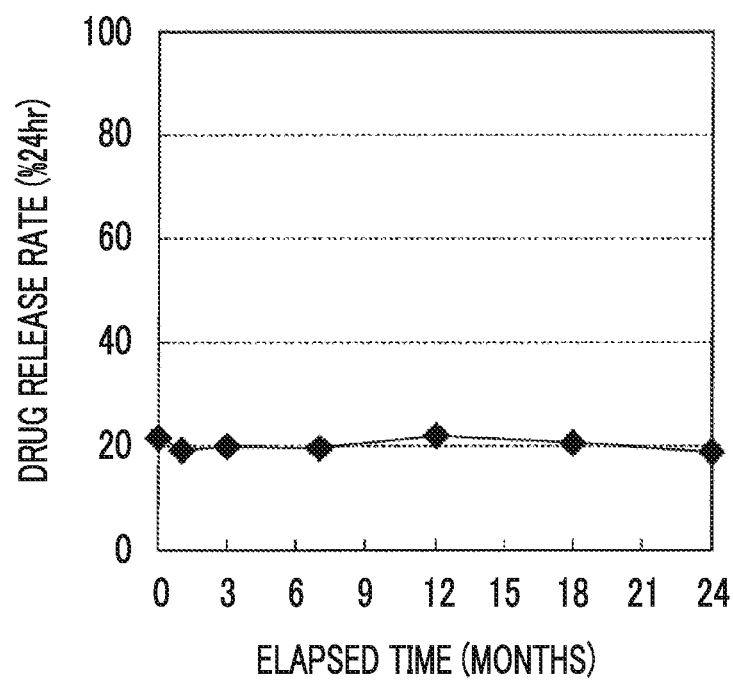
FIG. 6 is a plot of a relationship between a drug release rate and the elapsed time.

The results are shown in FIG. 6.

Surprisingly, it was found that there was almost no change in the drug release rate over an extended period of 24 months.

What is claimed is:

1. A method for producing a liposome composition, comprising:

an emulsifying step comprising emulsifying lipids dissolved in an organic solvent to form empty liposomes, without a drying and solidifying step, wherein the emulsifying lipids comprise a combination of hydrogenated soybean phosphatidylcholine as a main lipid, 1,2-distearoyl-3-phosphatidylethanolamine-polyethylene glycol, and cholesterol, and wherein the organic solvent is a mixture of ethanol and ethyl acetate;

a drug loading step comprising mixing and heating at a temperature higher than or equal to 50° C. an aqueous medium wherein gemcitabine is dissolved and the empty liposomes obtained in the emulsifying step to encapsulate the gemcitabine in the liposome, wherein the aqueous medium include at least one selected from the group consisting of inorganic salts, polyols and sugars, and is from 400 to 3200 mOsmol/L; and an adjusting step of the osmotic pressure of an outer water phase comprising removal of gemcitabine in the outer water phase and lowering of the outer water phase osmotic pressure to from 200 to 400 mOsmol/L by dialysis so that the osmotic pressure of an inner water phase of the liposome becomes 2-fold to 8-fold higher than the osmotic pressure of the outer water phase; and the mixing ratio of ethanol:ethyl acetate is 80:20 to 70:30 by mass ratio.

2. The method for producing a liposome composition according to claim 1, wherein there is no extrusion processing between the emulsifying step and the drug loading step.

* * * * *